United States Patent [19]

Lüning

[11] 4,107,298

[45] Aug. 15, 1978

[54] ANTIGENICALLY ACTIVE POLYPEPTIDE AND A PROCESS FOR ITS PREPARATION

[75] Inventor: Björn Erik Gustav Bertilsson Lüning, Stockholm, Sweden

[73] Assignee: AB Bonnierforetagen, Stockholm, Sweden

[21] Appl. No.: 789,665

[22] Filed: Apr. 21, 1977

[30] Foreign Application Priority Data

Apr. 29, 1976 [SE] Sweden ............................. 7604972

[51] Int. Cl.$^2$ ..................... A61K 37/00; C07C 103/52
[52] U.S. Cl. ............................ 424/177; 260/112.5 R
[58] Field of Search ................... 260/112.5 R; 424/177

[56] References Cited

U.S. PATENT DOCUMENTS

| | | | |
|---|---|---|---|
| 3,715,190 | 2/1973 | Won Kil Park et al. | 260/112.5 R |
| 3,929,756 | 12/1975 | Leeman et al. | 260/112.5 R |
| 3,960,827 | 6/1976 | Björklund | 424/177 |
| 4,018,753 | 4/1977 | Inouye et al. | 260/112.5 R |

FOREIGN PATENT DOCUMENTS

| | | | |
|---|---|---|---|
| 787,918 | 6/1968 | Canada | 260/112.5 R |
| 728,129 | 2/1966 | Canada | 260/112.5 R |

*Primary Examiner*—Delbert R. Phillips
*Attorney, Agent, or Firm*—Gordon W. Hueschen

[57] ABSTRACT

The invention provides for a synthetic antigenically active polypeptide containing an immunologically inert portion and as an active immunological determinant group the amino acid sequence $A_{-3}$-$A_{-2}$-$A_{-1}$-$A_0$-$A_1$-$A_2$-$A_3$, wherein $A_0$ is an arginine residue, $A_1$, $A_2$, $A_{-1}$ and $A_{-2}$ are the same or different and selected from residues of: glycine, alanine, valine, leucine, lysine, and isoleucine and $A_3$ and $A_{-3}$ are same or different and selected from glutamic acid and aspartic acid. The invention also provides for a process for the preparation of such polypeptide.

12 Claims, 1 Drawing Figure

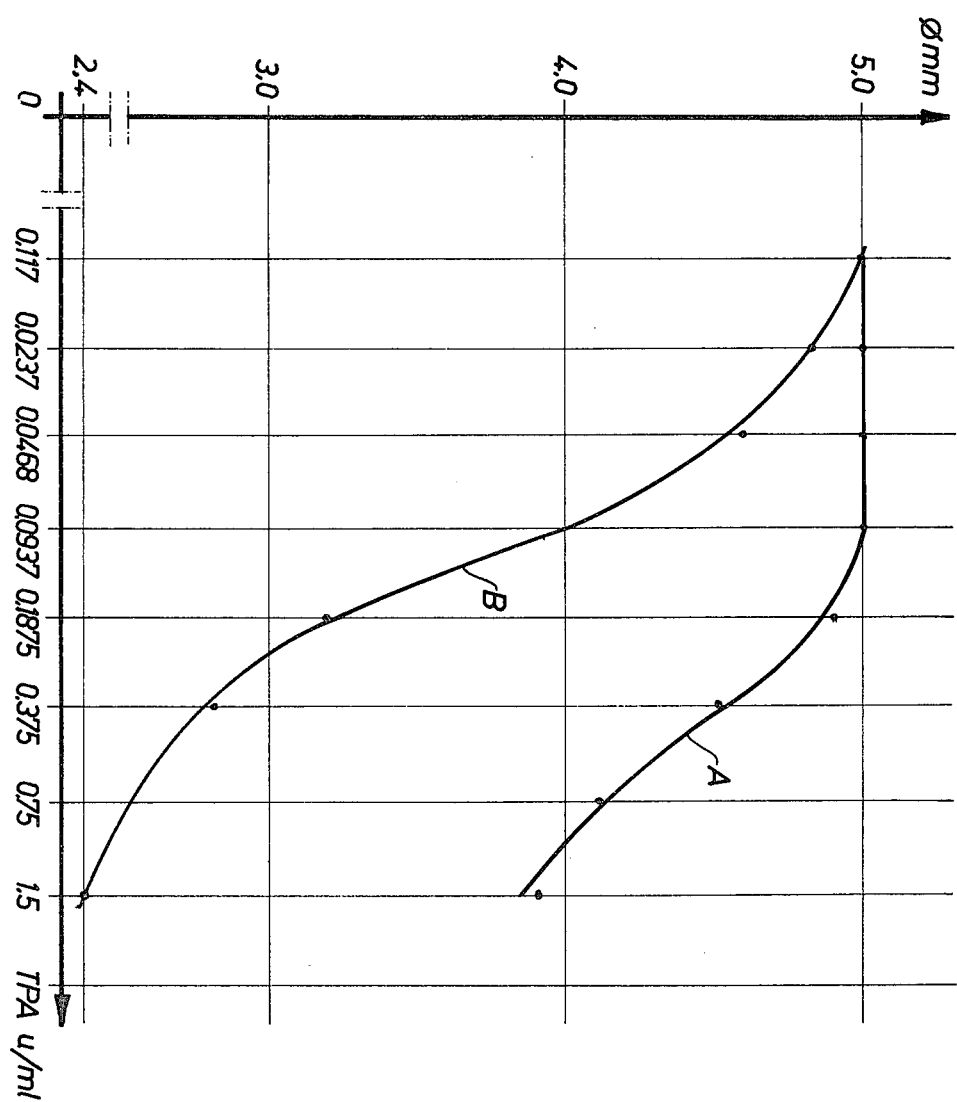

ANTIGENICALLY ACTIVE POLYPEPTIDE AND A PROCESS FOR ITS PREPARATION

The present invention relates to a synthetic antigenically active polypeptide which is characterized by containing an immunologically inert portion and as an immunologically determinant group, a certain aminoacid sequence, and a process for the preparation of said polypeptide.

In Swedish Pat. application 73-08917-9 and in U.S. Pat. No. 3,960,827 there is described a cancer-associated polypeptide antigen (CAPA), the technique for its isolation and its use in cancer diagnosis and in the preparation of antibodies. The CAPA is now commercialized under the designation TPA, which stands for "tissue polypeptide antigen". As is clear from the specification of the above-identified patent application and U.S. patent, the isolation of the natural antigen is a complicated procedure which, even if resulting in a practically useful product, still involves high production costs and moreover may involve difficulties in the provision of necessary starting materials, such as tumor tissue, etc. Against this background a synthetically prepared antigen would, of course, be very attractive, in view of the possibility of thereby obtaining a product exactly specified as to its composition, said product also being capable of being prepared at a more favorable price.

Referring to the drawing, the FIGURE shows in the hemagglutination inhibition test, comparison between the natural CAPA and the representative synthetic antigen of this invention according to Example 1. This FIGURE will be further explained hereinafter.

The main object of this invention is thus to provide a synthetic antigenically active polypeptide which reacts monospecifically with antibodies prepared by means of the polypeptide antigen described in the above-identified patent application.

According to one aspect of the instant invention, there is thus provided a synthetic antigenically active polypeptide characterized by containing as an active constituent or immunological determinative group the amino acid sequence: (I) $A_{-3}\text{-}A_{-2}\text{-}A_{-1}\text{-}A_0\text{-}A_1\text{-}A_2\text{-}A_3$, wherein $A_0$ indicates an arginine residue $A_1$, $A_2$, $A_{-1}$ and $A_{-2}$ are the same or different and are selected from aminoacid residues derived from glycine, alanine, valine, leucine, lysine and isoleucine. $A_3$ and $A_{-3}$ are the same or different and selected from residues derived from glutamic acid and aspartic acid.

As is clear from the above aminoacid sequence, the two fractions flanking the centrally positioned arginine residue indicated $A_0$ are mirror-images of each other, in that the two aminoacid residues adjacent to $A_0$ originate from neutral aminoacids, namely glycine, alanine, valine, leucine and isoleucine. Moreover, the aminoacid residues indicated by $A_3$ and $A_{-3}$, respectively, are derived from negative or acidic aminoacids, namely glutamic acid and aspartic acid, respectively. The obligatory arginine residue is moreover derived from a positive or basic aminoacid, namely arginine, the basicity of which, however, is superseded by the combined acidities of the aminoacid residues indicated by $A_3$ and $A_{-3}$. Thus, the aminoacid fraction imparting the desired antigenic activity to the polypeptide will thus, taken as a whole, have a negative or acidic character.

According to a preferred embodiment of the instant invention, the polypeptide contains the aminoacid sequence: (II) $A_{-4}\text{-}A_{-3}\text{-}A_{-2}\text{-}A_{-1}\text{-}A_0\text{-}A_1\text{-}A_2\text{-}A_3\text{-}A_4$, wherein $A_4$ and $A_{-4}$ are the same or different and selected from residues originating from glycine, alanine, valine, leucine and isoleucine which, as indicated above, are neutral aminoacids. In view of the character of the aminoacids in said respect, the fractions of the aminoacid sequence flanking the centrally positioned arginine residue indicated $A_0$ are still mirror-images of each other. Other symbols in this preferred aminoacid sequence have the meanings given above.

(III) According to a particularly preferred embodiment of the present invention, a tyrosine residue is attached to the aminoacid residue $A_{-4}$, said tyrosine residue, as is clear from the following description, playing a relatively essential role for the activity of the product. The sequence $A_{-4}$ through $A_0$ is most important in this embodiment.

(IV) In the last-mentioned embodiment containing a tyrosine residue $A_1$ and $A_4$ are preferably alanine residues, $A_2$, $A_{-2}$ and $A_{-4}$ are leucine residues, and $A_3$ a glutamic acid residue, $A_{-1}$ being a valine residue and $A_{-3}$ an aspartic acid residue.

From hereon the following abbreviations for the aminoacids in question are used:

| | | | |
|---|---|---|---|
| ALANINE | Ala | | |
| ARGININE | Arg | | |
| ASPARAGINE | Asn | | |
| ASPARTIC ACID | Asp | | |
| GLUTAMINE | Gln | | |
| GLUTAMIC ACID | Glu | | |
| GLYCINE | GLY | | |
| ISOLEUCINE | Ile | | |
| LEUCINE | Leu | THREONINE | Thr |
| TYROSINE | Tyr | PHENYLALANINE | Phe |
| VALINE | Val | LYSINE | Lys |

Using the above abbreviations, in a particularly preferred embodiment $A_5$ is an alanine residue, and $A_6$ and $A_{-6}$ are the same or different and selected from residues of glutamine and asparagine. In this aminoacid sequence, the following specific sequence is particularly preferred: (V) Gln-Tyr-Leu-Asp-Leu-Val-Arg-Ala-Leu-Glu-Ala-Ala-Asn.

Moreover, it is preferred in this sequence at both ends thereof to connect as $A_7$ a glycine residue and as $A_{-7}$ an alanine residue, i.e., using the above abbreviations the sequence: (VI) Ala-Gln-Tyr-Leu-Asp-Leu-Val-Arg-Ala-Leu-Glu-Ala-Ala-Asn-Gly.

In the foregoing formulas V and VI Gln may be replaced equally well by lysine or Asn, or vice versa.

The present invention also relates to a process for the preparation of the antigenically active polypeptide, and in this process an N-protected amino acid is attached to a resin by esterification, the N-protecting group is removed and a second N-protected amino acid is coupled to the amino group of the resin-bound amino acid, the N-protecting group is removed and the coupling step is repeated with a third N-protected amino acid. Protecting groups in the process are the usual groups, and are set forth more fully in the following. This procedure is repeated until the desired amino acid sequence is obtained, the polypeptide being then cleaved from the resin. It is preferred after each attachment of an N-protected amino acid to the resin-bound amino acid to wash away all by products and unreacted soluble materials.

The resin used in the synthesis may consist of a copolymer of styrene and divinyl benzene, the styrene constituting the major part of the copolymer, for instance about 98% of styrene and about 2% of divinyl benzene.

In order to provide a reactive group for coupling to the first amino acid, the benzene rings are suitably partially chloromethylated. When this chloromethylated resin is treated with the triethylamine salt of an N-protected amino acid, a bond of the benzyl ester type is formed. Such bond is stable under the synthesis steps, but can be cleaved with HBr in acetic acid or trifluoroacetic acid, the N-protecting group being simultaneously removed and the peptide separated from the resin.

In order to protect the amino acid the t-butyloxycarbonyl group can suitably be used as it is conveniently cleaved by means of HCl in acetic acid. It is also possible to use the carbobenzoxy group for the purpose, but in this case HBr in acetic acid must be used for removal of the protecting group. As a protecting group there may also be used the o-nitrophenyl sulfenyl group. Other protecting groups may also be employed and will be apparent to one skilled in the art.

The coupling reagent most frequently used in the synthesis is dicyclohexylcarbodiimide. If methylene chloride is used as a solvent and about 50% excess of t-butyloxy carbonyl aminoacid and dicyclohexyl carbodiimide, a quantitative reaction is obtained within a few minutes. Even dimethylformamide may be used as a solvent. As regards further details regarding the synthesis procedure reference is had to the book "Protein Sequence Determination" summarized by Saul. B. Needleman, Springer-Verlag, Berlin-Heidelberg-New York, 1970, particularly pp. 308–310. Other coupling agents are also suitable and will be apparent to one skilled in this art.

The present invention will now be illustrated further by means of non-limiting examples.

EXAMPLE 1

By the process in solid phase according to Merrifield (cf. the above literature reference) the following product is prepared:

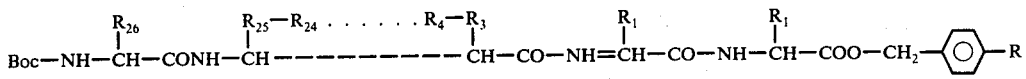

wherein: R indicates the resin part; Boc is a t-butyloxy carbonyl group;

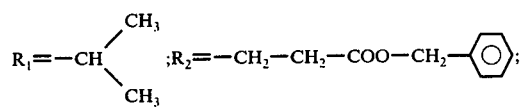

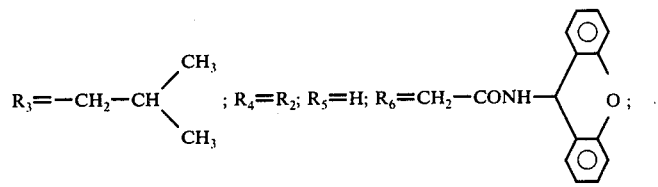

$R_7=CH_3$; $R_8=R_7$; $R_9=R_2$; $R_{10}=R_3$; $R_{11}=R_7$;

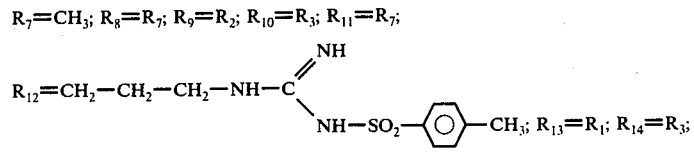

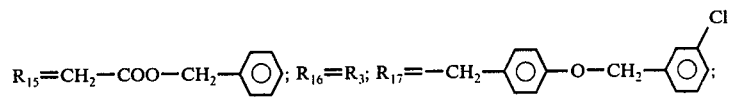

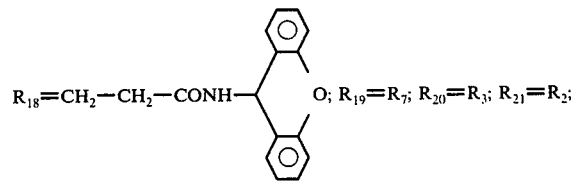

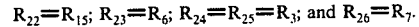

The amino acid sequence between the t-butyloxycarbonyl group and the resin part may be expressed in the following manner using the foregoing abbreviations regarding the amino acids:

Ala Leu Leu Asn Asp Glu Leu Ala Gln Tyr Leu Asp
Leu Val Arg Ala Leu Glu Ala Ala Asn Gly Gln
Leu Glu Val  (VII)

0.4 mmole of Boc-valine (resinbenzyl ester) was transferred to the cuvette of a Beckman peptide synthesizer and swollen in methylene chloride ($CH_2Cl_2$). The protecting Boc-group was removed by treatment with trifluoroacetic acid in excess in methylene chloride. After washing with methylene chloride the resin was neutralized with triethylamine and again washed with methylene chloride. N-Boc-glutamic acid benzyl ester (coupling step 1) and cyclohexylcarbodiimide was added dissolved in $CH_2Cl_2$, and the mixture was stirred for 30 minutes. The resin was washed and the coupling step repeated. This terminates the introduction of $R_2$ in step 1 according to the above.

Step 2 of the synthesis starts by removal of an N-Boc from the N-terminated amino acid and repetition of the coupling step while using another N-Boc-amino acid. To build up the above amino acid sequence the following reagents are used in the subsequent steps:

| in step | 2: | N-Boc-Leucine |
|---|---|---|
| " | 3: | D:o as in step 1 |
| " | 4: | N-Boc-glycine |
| " | 5: | N-Boc-asparagine-xanthydryl derivative |
| " | 6: | N-Boc-alanine |
| " | 7: | D:o as in step 6 |
| " | 8: | D:o as in step 1 |
| " | 9: | D:o as in step 2 |
| " | 10: | D:o as in step 6 |
| " | 11: | N-Boc-G-tosylargine |
| " | 12: | N-Boc-valine |
| " | 13: | D:o as in step 2 |
| " | 14: | N-Boc-aspartic acid benzyl ester |
| " | 15: | D:o as in step 2 |
| " | 16: | N-Boc-tyrosine-3-chlorobenzyl ether |
| " | 17: | N-Boc-glutamine-xanthydryl derivative |
| " | 18: | D:o as in step 6 |
| " | 19: | D:o as in step 2 |
| " | 20: | D:o as in step 1 |
| " | 21: | D:o as in step 14 |
| " | 22: | D:o as in step 5 |
| " | 23: | D:o as in step 2 |
| " | 24: | D:o as in step 2 |
| " | 25: | D:o as in step 6 |

The protecting groups are removed from the protected resin-bond peptide and the resin is cleaved off by using anhydrous hydrogen fluoride at 0° C for 30 minutes, and the peptide is extracted from the resin by means of a 10% aqueous solution of acetic acid. After evaporation the residue is purified by gel filtration on Sephadex G 25 Fine in 0.1 M $NH_4HCO_3$. After lyophilization of the peptide a satisfactory amino acid analysis is obtained, together with a molecular weight of approximately 3000, as determined by gel filtration. The theoretical MW value is 2959.71.

The polypeptide prepared according to the foregoing was investigated with regard to its ability to inhibit the hemagglutination reaction between tanned red sheep blood cells labelled with natural cancer antigen and antibodies prepared by using natural cancer antigen (CAPA or TPA). With regard to details concerning this technique reference is had to the above-identified Swedish patent application 73-08917-9 and U.S. Pat. No. 3,960,827. The specific activity of the polypeptide was found to be 0.024 Units per milligram (U/mg). Said Unit for specific activity is defined as 1/6 of the quantity active polypeptide required to label $10^9$ sheep blood cells so as to be fully agglutinated by a minimum number or amount of antibodies (maximum dilution of antibodies).

For the purpose of investigating what functions that are critical for the activity of the polypeptide, the basic structure of which is given above, certain experiments were carried out. The centrally positioned arginine indicated by $A_0$ was thus blocked with cyclohexanedione at pH 13 resulting in 99.5% loss of activity. If, however, the polypeptide is subjected only to a basic environment, wherein the pH is 13 for the same period of time, the activity is lowered only by about 20%. This indicates the fact that the arginine presence in the polypeptide according to the present invention is of decisive importance for the antigenic activity.

For the purpose of investigating the effect of the tyrosine designated $A_{-5}$, the polypeptide was treated with iodine at pH 9.5. When using iodine in an excess of about 10000 times in relation to the tyrosine content of the polypeptide, about 85% of the activity is lost, at 1000 times excess about 75% of the activity is lost, whereas at 100 times excess 40-50% of the activity disappears. At an excess of only about 10 times the activity of the polypeptide is, however, not effected.

From the character of the basic structure, it is clear that the polypeptide has an acidic character, thus being negatively charged in a neutral solution while, however, maintaining the positive charge of the arginine part thereof.

The chemical basis for the antigenic character of the polypeptide has thus been set forth in the foregoing description. The remarkable specific activity which has been obtained by means of a synthetically prepared product, the activity of which can be said to be of a haptenic nature, due to the small determinant group, constitutes a pioneering advance with regard to the application of immunology and testing, i.e. diagnosis, within the cancer area.

Clearly and in accordance with what is known in immunology, antigenic activity is a function not only of the structure of the haptenic determinant group, but also of the size of the polypeptide. Said size does not, however, effect the specificity of the peptide but only the degree of activity, inasmuch as a larger molecule tends to be more active than a smaller one. Therefore, an improved activity is obtained if the polypeptide is arranged on a suitable immunogenically active carrier, for instance a protein, such as albumin, for instance egg white. Already the polypeptide in its basic structural form, i.e., having at least 7 amino acid units, does, however, show an antigenic activity which is sufficient to enable the polypeptide to react with corresponding antibodies. Moreover, the polypeptide may be used for generating antibodies; however, this calls for coupling the polypeptide to a suitable protein acting as a carrier or so-called "Schlepperantigene," for instance swine serum. Thus, the activity is imparted to the polypeptide chain beginning at as low as 7 and especially 9 amino acid units, appears to be maximized at about 26 amino acid units, and is still present at in excess of thirty amino acid units, the portion of the polypeptide chain not being an immunological determinant group as hereinbefore defined being inert immunologically but serving to provide a "carrier" for the immunologically determinant groups.

The present invention is in no way limited to the foregoing specific embodiments. Thus, in preparing the polypeptide, the resin may be any material containing benzene rings and in addition at least one group having the ability of binding N-protected amino acids by esterification. The ester bond must be relatively easy to hydrolyse and, of course, must be easier to cleave than the peptide bonds in the polypeptide. However, the ester bond must be sufficiently stable to be able to withstand the reaction conditions under the synthesis.

As an alternative to the above mentioned coupling reagent, dicyclohexyl carbodiimide, when attaching glutamine and asparagine units, coupling may instead be carried out with so-called active esters, for instance cyanomethyl, thiophenyl or nitrophenyl esters. As a solvent in the synthesis so-called aprotic solvents are suitable, particularly solvents that are somewhat hydrophilic or "semipolar."

Regarding useful groups to protect the N-amino acids, it is noted that t-butyloxy carbonyl groups, wherein one or two methyl groups are replaced by phenyl, also may be advantageously used. In this connection it can be mentioned that the product obtained in the synthesis is provided with N-protecting groups and attached to a resin by esterification, and that it advantageously can be stored for a long period of time without being destroyed. In connection with the use of the polypeptide, the protecting groups and the resin part may then be removed.

In the amino acid sequences given in the present preparation, the terminal groups (after removal of the protecting groups and the resin part) are always amino group and carboxyl group, respectively. The amino group is found at the end of the chain wherein the symbols A are designated minus, whereas the carboxyl group is found at the opposite end of the amino acid sequence.

In Example 1 as described above the antigenic activity of the synthesized polypeptide was determined in the following manner.

For quantitative determination of the amount of polypeptide 7 mgs of the peptide are dissolved in 1.4 mls of buffer grade serum, i.e. a physiological saline solution containing 2% of inert human serum and buffered to a pH of about 7.5 with a phosphate buffer. Under serial dilution a series of samples of said solution having a decreasing polypeptide concentration is prepared and to each of said samples there is added a pre-determined amount of anti-serum containing antibodies specific to TPA. To each of the resulting samples there is then added, after incubation, a predetermined amount of the polypeptide carried on a particulate carrier, hemagglutination taking place to an extent corresponding to the amount of available antibodies. In parallel there is prepared a corresponding series of control samples containing known decreasing amounts of TPA. The diameters of the hemagglutination depositions of the control samples are then measured in their respective cavities on a serial dilution test plate, and the values of the diameters obtained are plotted against the TPA concentrations, an S-shaped curve being obtained, the intermediate part of which including an inflexion point as a steep inclination. The corresponding curve of the diameter of the depositions from the hemagglutination as a function of the TPA-concentrations is shown in the diagram of the appended drawing, as curve B.

In the same diagram the corresponding curve for the synthesized polypeptide is shown as A, and with knowledge of the specific activity of the TPA the specific activity of the synthesized polypeptide is found to be 0.024 Units per milligram of peptide.

EXAMPLE 2

In the same manner as given in Example 1 the following polypeptide is prepared and found to be about equally immunologically active as the polypeptide of Example 1:

| Thr | Asp | Leu | Asp | Asp | Arg | Leu |
| Ala | Lys | Tyr | Leu | Asp | Lys | Val |
| Arg | Ala | Leu | Glu | Ala | Ala | Asp |
| Gly | Glu | Leu | Glu | Val | | |

EXAMPLE 3

In the same manner as given in Example 1 the following polypeptide is prepared and found to be about equally immunologically active as the polypeptide of Example 1:

| Ala | Gln | Tyr | Leu | Asp | Leu | Val | Arg | Ala | Leu |
| Glu | Ala | Ala | Asn | Gly | Glu | Leu | Glu | Val | |

When this determinant group is coupled to inert bovine albumin in a molar ratio of about 1:1 by means of a water soluble carbodiimide (EDC) the immunological activity of the peptide is maintained.

EXAMPLE 4

In the same manner as given in Example 1 the following polypeptide is prepared and found to be about equally immunologically active as the polypeptide of Example 1:

| Leu | Asn | Asp | Glu | Leu | Ala | Gln | Tyr | Leu | Asp | Leu | Val |
| Arg | Ala | Leu | Glu | Ala | Ala | Asn | Gly | Arg | Leu | Glu | Val |

When coupled to inert albumin in the same way as described in Example 3, the activity was maintained.

EXAMPLE 5

In the same manner as given in Example 1 the following polypeptide is prepared and found to be about equally immunologically active as the polypeptide of Example 1:

| Asn | Asp | Ile | Leu | Ala | Gln | Tyr | Leu | Asp | Leu | Val |
| Arg | Ala | Leu | Glu | Ala | Ala | Asn | Gly | | | |

EXAMPLE 6

In the same manner as given in Example 1 the following polypeptide is prepared and found to be about equally immunologically active as the polypeptide of Example 1:

| Asp | Asp | Arg | Leu | Ala | Lys | Tyr | Leu | Asp | Lys | Val |
| Arg | Ala | Leu | Glu | Ala | Ala | Asp | Gly | | | |

EXAMPLES 7–22.

In the same manner as given in Example 1 the following polypeptides are prepared and found to be about equally immunologically active as the polypeptide of Example 1.

| | | | | | | | | | | | | | | | | | | | | |
|---|---|---|---|---|---|---|---|---|---|---|---|---|---|---|---|---|---|---|---|---|
| Ex. 7 | Leu | Asn | Asp | Arg | Leu | Ala | Lys | Tyr | Leu | Asp | Lys | Val | Arg | Ala | Leu | Glu | Ala | Ala | Asn | Gly | Glu Leu Glu Val |
| Ex. 8 | Leu | Asn | Asp | Glu | Leu | Ala | Lys | Tyr | Leu | Asp | Lys | Val | Arg | Ala | Leu | Glu | Ala | Ala | Asn | Gly | Glu Leu Glu Val |
| Ex. 9 | Leu | Asn | Asp | Arg | Leu | Ala | Gln | Tyr | Leu | Asp | Lys | Val | Arg | Ala | Leu | Glu | Ala | Ala | Asn | Gly | Glu Leu Glu Val |
| Ex.10 | Leu | Asn | Asp | Glu | Leu | Ala | Gln | Tyr | Leu | Asp | Lys | Val | Arg | Ala | Leu | Glu | Ala | Ala | Asn | Gly | Glu Leu Glu Val |
| Ex.11 | Leu | Asn | Asp | Arg | Leu | Ala | Lys | Tyr | Leu | Asp | Leu | Val | Arg | Ala | Leu | Glu | Ala | Ala | Asn | Gly | Glu Leu Glu Val |
| Ex.12 | Leu | Asn | Asp | Glu | Leu | Ala | Lys | Tyr | Leu | Asp | Leu | Val | Arg | Ala | Leu | Glu | Ala | Ala | Asn | Gly | Glu Leu Glu Val |
| Ex.13 | Leu | Asn | Asp | Arg | Leu | Ala | Gln | Tyr | Leu | Asp | Leu | Val | Arg | Ala | Leu | Glu | Ala | Ala | Asn | Gly | Glu Leu Glu Val |
| Ex.14 | Leu | Asn | Asp | Glu | Leu | Ala | Gln | Tyr | Leu | Asp | Leu | Val | Arg | Ala | Leu | Glu | Ala | Ala | Asn | Gly | Glu Leu Glu Val |
| Ex.15 | Leu | Asn | Asp | Arg | Leu | Ala | Lys | Tyr | Leu | Asp | Lys | Val | Arg | Ala | Leu | Glu | Ala | Ala | Asn | Gly | Arg Leu Glu Val |
| Ex.16 | Leu | Asn | Asp | Glu | Leu | Ala | Lys | Tyr | Leu | Asp | Lys | Val | Arg | Ala | Leu | Glu | Ala | Ala | Asn | Gly | Arg Leu Glu Val |
| Ex.17 | Leu | Asn | Asp | Arg | Leu | Ala | Gln | Tyr | Leu | Asp | Lys | Val | Arg | Ala | Leu | Glu | Ala | Ala | Asn | Gly | Arg Leu Glu Val |
| Ex.18 | Leu | Asn | Asp | Glu | Leu | Ala | Gln | Tyr | Leu | Asp | Lys | Val | Arg | Ala | Leu | Glu | Ala | Ala | Asn | Gly | Arg Leu Glu Val |
| Ex.19 | Leu | Asn | Asp | Arg | Leu | Ala | Lys | Tyr | Leu | Asp | Leu | Val | Arg | Ala | Leu | Glu | Ala | Ala | Asn | Gly | Arg Leu Glu Val |
| Ex.20 | Leu | Asn | Asp | Glu | Leu | Ala | Lys | Tyr | Leu | Asp | Leu | Val | Arg | Ala | Leu | Glu | Ala | Ala | Asn | Gly | Arg Leu Glu Val |
| Ex.21 | Leu | Asn | Asp | Arg | Leu | Ala | Gln | Tyr | Leu | Asp | Leu | Val | Arg | Ala | Leu | Glu | Ala | Ala | Asn | Gly | Arg Leu Glu Val |
| Ex.22 | Leu | Asn | Asp | Glu | Leu | Ala | Gln | Tyr | Leu | Asp | Leu | Val | Arg | Ala | Leu | Glu | Ala | Ala | Asn | Gly | Arg Leu Glu Val |

EXAMPLE 23

In the same manner as given in Example 1 the following polypeptide is prepared and found to be about equally immunologically active as the polypeptide of Example 1

| Thr | Asp | Leu | Asp | Asp | Arg | Leu | Ala | Lys | Tyr | Leu | Asp | Lys |
| Val | Arg | Ala | Leu | Glu | Ala | Ala | Asp | Gly | Glu | Leu | Glu | Val |
| | Phe | Asp | Glu | Leu | Asn | Leu | Gln | | | | | |

EXAMPLE 24

In the same manner as given in Example 1 the following polypeptide is prepared and found to be about equally immunologically active as the polypeptide of Example 1

| Ala | Leu | Leu | Asn | Asp | Glu | Leu | Ala | Gln | Tyr | Leu | Asp | Leu | Val |
| Arg | Ala | Leu | Glu | Ala | Ala | Asn | Gly | Arg | Leu | Glu | Val | Phe | Asp |
| Glu | Leu | Asn | Leu | Gln | | | | | | | | | |

EXAMPLE 25

In the same manner as given in Example 1 the following polypeptide is prepared and found to be about equally immunologically active as the polypeptide of Example 1

| Ala | Leu | Leu | Asn | Asp | Ile | Leu | Ala | Gln | Tyr | Leu | Asp | Leu | Val |
| Arg | Ala | Leu | Glu | Ala | Ala | Asn | Gly | Arg | Leu | Glu | Val | | |

Various modifications and substitutions of equivalents may be made in the products, process, conditions, and procedures of the present invention and will be immediately apparent to one skilled in the art, wherefore the invention is to be limited only by the full scope of the appended claims, including application of the doctrine of equivalents thereto.

What is claimed is:

1. Synthetic antigenically active polypeptide, characterized by containing an immunologically inert portion and as an active immunological determinant group the amino acid sequence: $A_{-3}\text{-}A_{-2}\text{-}A_{-1}\text{-}A_0\text{-}A_1\text{-}A_2\text{-}A_3$, wherein $A_0$ is an arginine residue, $A_1$, $A_2$, $A_{-1}$ and $A_{-2}$ are same or different and selected from residues of: glycine, alanine, valine, leucine, lysine, and isoleucine and $A_3$ and $A_{-3}$ are same or different and selected from glutamic acid and aspartic acid.

2. A polypeptide according to claim 1, characterized in that the amino acid sequence is: $A_{-3}\text{-}A_{-2}\text{-}A_{-1}\text{-}A_0\text{-}A_1\text{-}A_2\text{-}A_3$, wherein $A_0$ is an arginine residue, $A_1$, $A_2$, $A_{-1}$ and $A_{-2}$ are same or different and selected from residues of: glycine, alanine, valine, leucine, and isoleucine and $A_3$ and $A_{-3}$ are same or different and selected from glutamic acid and aspartic acid.

3. Synthetic antigenically active polypeptide, characterized by containing an immunologically inert portion and as an active immunological determinant group the amino acid sequence: $A_{-4}\text{-}A_{-3}\text{-}A_{-2}\text{-}A_{-1}\text{-}A_0\text{-}A_1\text{-}A_2\text{-}A_3\text{-}A_4$, wherein $A_0$ is an arginine residue, $A_1$, $A_2$, $A_{-1}$ and $A_{-2}$ are same or different and selected from residues of: glycine, alanine, valine, leucine, lysine, and isoleucine and $A_3$ and $A_{-3}$ are same or different and selected from glutamic acid and aspartic acid, and $A_4$ and $A_{-4}$ are same or different and selected from glycine, alanine, valine, leucine, and isoleucine.

4. Synthetic antigenically active polypeptide, characterized by containing an immunologically inert portion and as an active immunological determinant group the amino acid sequence: $A_{-5}\text{-}A_{-4}\text{-}A_{-3}\text{-}A_{-2}\text{-}A_{-1}\text{-}A_0\text{-}A_1\text{-}A_2\text{-}A_3\text{-}A_4$, wherein $A_{-5}$ is a tyrosine residue and wherein $A_0$ is an arginine residue, $A_1$, $A_2$, $A_{-1}$ and $A_{-2}$ are same or different and selected from residues of: glycine, alanine, valine, leucine, lysine, and isoleucine and $A_3$ and $A_{-3}$ are same or different and selected from glutamic acid and aspartic acid, and wherein $A_4$ and $A_{-4}$ are same or different and selected from glycine, alanine, valine, leucine and isoleucine.

5. A polypeptide according to claim 4, characterized in that $A_1$ and $A_4$ are alanine residues, $A_2$, $A_{-2}$ and $A_{-4}$ are leucine residues and $A_3$ is a glutamic acid residue, $A_{-1}$ is a valine residue and $A_{-3}$ is an aspartic acid residue.

6. Synthetic antigenically active polypeptide, characterized by containing an immunologically inert portion and as an active immunological determinant group the amino acid sequence: $A_{-6}\text{-}A_{-5}\text{-}A_{-4}\text{-}A_{-3}\text{-}A_{-2}\text{-}A_{-1}\text{-}A_0\text{-}A_1\text{-}A_2\text{-}A_3\text{-}A_4\text{-}A_5\text{-}A_6$, characterized in that $A_1$ and $A_4$ and $A_5$ are alanine residues, $A_2$, $A_{-2}$ and $A_{-4}$ are leucine residues and $A_3$ is a glutamic acid residue, $A_{-1}$ is a valine residue and $A_{-3}$ is an aspartic acid residue, $A_0$ is an arginine residue, $A_{-5}$ is a tyrosine residue, and $A_6$ and $A_{-6}$ are same or different and selected from residues of glutamine, asparagine, and lysine.

7. A polypeptide according to claim 6, wherein $A_6$ and $A_{-6}$ are same or different and selected from residues of glutamine and asparagine.

8. A polypeptide according to claim 6, characterized in that $A_6$ is an asparagine residue and $A_{-6}$ a glutamine residue.

9. Synthetic antigenically active polypeptide, characterized by containing an immunologically inert portion and as an active immunological determinant group the amino acid sequence: $A_{-7}\text{-}A_{-6}\text{-}A_{-5}\text{-}A_{-4}\text{-}A_{-3}\text{-}A_{-2}\text{-}A_{-1}\text{-}A_0\text{-}A_1\text{-}A_2\text{-}A_3\text{-}A_4\text{-}A_5\text{-}A_6\text{-}A_7$, characterized in that $A_1$ and $A_4$ and $A_5$ are alanine residues, $A_2$, $A_{-2}$ and $A_{-4}$ are leucine residues and $A_3$ is a glutamic acid residue, $A_{-1}$ is a valine residue and $A_{-3}$ is an aspartic acid residue, $A_0$ is an arginine residue, $A_{-5}$ is a tyrosine residue, $A_6$ is an asparagine residue and $A_{-6}$ a glutamine residue, and wherein $A_7$ is a glycine residue and $A_{-7}$ an alanine residue.

10. Synthetic antigenically active polypeptide, characterized by containing an immunologically inert portion and as an active immunological determinant group the amino acid sequence: Ala Leu Leu Asn Asp Glu Leu Ala Gln Tyr Leu Asp Leu Val Arg Ala Leu Glu Ala Ala Asn Gly Glu Leu Glu Val.

11. Synthetic antigenically active polypeptide, characterized by containing an immunologically inert portion and as an active immunological determinant group the amino acid sequence: Thr Asp Leu Asp Asp Arg Leu Ala Lys Tyr Leu Asp Lys Val Arg Ala Leu Glu Ala Ala Asp Gly Glu Leu Glu Val.

12. Synthetic antigenically active polypeptide, characterized by containing an immunologically inert portion and as an active immunological determinant group the amino acid sequence: Leu Asn Asp $A_{-9}$ Leu Ala $A_{-6}$ Tyr Leu Asp $A_{-2}$ Val Arg Ala Leu Glu Ala Ala Asn Gly $A_8$ Leu Glu Val, wherein $A_{-9}$ and $A_8$ are same or different and selected from residues of glutamic acid and arginine; $A_{-6}$ is selected from residues of glutamine and lysine; and $A_{-2}$ is selected from residues of leucine and lysine.

* * * * *

UNITED STATES PATENT AND TRADEMARK OFFICE
CERTIFICATE OF CORRECTION

PATENT NO. : 4,107,298

DATED : August 15, 1978

INVENTOR(S) : Lüning

It is certified that error appears in the above-identified patent and that said Letters Patent are hereby corrected as shown below:

Col. 5, line 21, Step 11 in the chart; "tosylargine" should read --tosylarginine--

Col. 11, line 10; "$A_6$" (2nd occurrence) should read --$A_{-6}$--.

Signed and Sealed this

Sixth Day of February 1979

[SEAL]

Attest:

RUTH C. MASON
Attesting Officer

DONALD W. BANNER
Commissioner of Patents and Trademarks